(12) United States Patent
Kojima et al.

(10) Patent No.: US 10,537,679 B2
(45) Date of Patent: Jan. 21, 2020

(54) LOCKING MEMBER, MIXING TIP, AND DOUBLE SYRINGE

(71) Applicant: GC Corporation, Tokyo (JP)

(72) Inventors: Shinichi Kojima, Tokyo (JP); Shigeru Chiba, Ibaraki (JP); Akihiro Fujii, Ibaraki (JP)

(73) Assignee: GC CORPORATION, Tokyo (JP)

( * ) Notice: Subject to any disclaimer, the term of this patent is extended or adjusted under 35 U.S.C. 154(b) by 252 days.

(21) Appl. No.: 15/329,277

(22) PCT Filed: Jul. 31, 2015

(86) PCT No.: PCT/JP2015/071863
§ 371 (c)(1),
(2) Date: Jan. 26, 2017

(87) PCT Pub. No.: WO2016/021515
PCT Pub. Date: Feb. 11, 2016

(65) Prior Publication Data
US 2017/0209645 A1    Jul. 27, 2017

(30) Foreign Application Priority Data
Aug. 4, 2014 (JP) .................................. 2014-158717

(51) Int. Cl.
*A61M 5/19* (2006.01)
*B01F 5/00* (2006.01)
(Continued)

(52) U.S. Cl.
CPC ................. *A61M 5/19* (2013.01); *B01F 5/00* (2013.01); *B01F 5/0614* (2013.01);
(Continued)

(58) Field of Classification Search
CPC .... A61M 5/19; A61M 5/2066; A61M 5/2488; A61M 5/284; A61M 5/6827;
(Continued)

(56) References Cited

U.S. PATENT DOCUMENTS 5,918,772 A    7/1999  Keller et al.
6,311,869 B1   11/2001 Hoerth et al.
(Continued)

FOREIGN PATENT DOCUMENTS

JP    H08-312237    11/1996
JP    H09-187637    7/1997
(Continued)

OTHER PUBLICATIONS

Patent translate: Translation of JP 2013027599 A, Mar. 9, 2018.*
International Search Report dated Sep. 29, 2015.

*Primary Examiner* — Nilay J Shah
(74) *Attorney, Agent, or Firm* — IPUSA, PLLC

(57) ABSTRACT

A locking member that locks a mixing nozzle to a cartridge that includes two syringes, the mixing nozzle being configured to mix the materials from the two syringes within the nozzle as the materials are discharged. The locking member includes a support rod supported on the mixing nozzle that is displaceable in a direction orthogonal to the direction in which the nozzle extends, and first and second engaging parts that engage with horizontal parts provided on the cartridge. The locking member further includes an inclined part that is inclined toward the opposite side to the nozzle, and that is provided between at least one of the first engaging part and the second engaging part, or between the second engaging part and the other end of the support rod.

4 Claims, 20 Drawing Sheets

(51) Int. Cl.
  *B01F 15/00* (2006.01)
  *B65D 41/16* (2006.01)
  *B01F 5/06* (2006.01)
  *B01F 13/00* (2006.01)
  *B05C 17/005* (2006.01)
  *A61M 3/00* (2006.01)
  *A61M 5/20* (2006.01)
  *A61M 39/10* (2006.01)
  *A61M 5/28* (2006.01)
  *A61M 5/315* (2006.01)

(52) U.S. Cl.
  CPC .......... *B01F 13/0023* (2013.01); *B01F 15/00* (2013.01); *B01F 15/0087* (2013.01); *B05C 17/00506* (2013.01); *B05C 17/00553* (2013.01); *B65D 41/16* (2013.01); *A61M 3/005* (2013.01); *A61M 5/2066* (2013.01); *A61M 5/284* (2013.01); *A61M 5/31596* (2013.01); *A61M 2039/1027* (2013.01); *B01F 2215/0034* (2013.01)

(58) Field of Classification Search
  CPC .............. A61M 5/31596; A61M 3/005; A61M 3/1407; A61M 3/1408; A61M 2039/1027; A61M 2039/1033; A61M 5/16827; A61M 39/10; B01F 5/0614; B01F 15/0087; B01F 13/0023; B01F 2215/0034; F16L 33/00; A61J 1/1418; A61J 1/1425; A61J 1/1481; A61J 1/1487
  See application file for complete search history.

(56) References Cited

U.S. PATENT DOCUMENTS

| | | |
|---|---|---|
| 2008/0089173 A1 | 4/2008 | Lu et al. |
| 2008/0173673 A1 | 7/2008 | Mueller-Paul |
| 2008/0232187 A1 | 9/2008 | Miyano et al. |
| 2009/0230214 A1 | 9/2009 | Keller |
| 2011/0306940 A1* | 12/2011 | Miyasaka .......... A61M 39/1011 604/256 |
| 2013/0008932 A1 | 1/2013 | Shindo |
| 2014/0124536 A1 | 5/2014 | Pappalardo |

FOREIGN PATENT DOCUMENTS

| | | |
|---|---|---|
| JP | 2001-124276 | 5/2001 |
| JP | 2003-137013 | 5/2003 |
| JP | 2008-229553 | 10/2008 |
| JP | 2009-537291 | 10/2009 |
| JP | 2013-014242 | 1/2013 |
| JP | 2013-027599 | 2/2013 |
| JP | 2013027599 A * | 2/2013 |

* cited by examiner

LOCKING MEMBER, MIXING TIP, AND DOUBLE SYRINGE

TECHNICAL FIELD

The present invention relates to a locking member, a mixing tip, and a double syringe.

BACKGROUND ART

There is known a two component mixing apparatus including a cartridge for accommodating different materials and two cylindrical containers, and a mixing tip that is coupled to the cartridge, and that mixes the materials that are extruded from the outlets of the cylindrical containers, and discharges the materials (see, for example, patent literature 1).

CITATION LIST

Patent Literature

[PTL 1]
Japanese Unexamined Patent Application Publication No. H09-187637

SUMMARY OF INVENTION

Technical Problem

In the two component mixing apparatus having the above configuration, in order to mix the materials by a predetermined ratio while preventing the materials from leaking outside, and to accurately discharge the mixed materials to a desired position, the mixing tip and the cartridge need to firmly coupled and fixed to each other. Furthermore, when the materials mixed in the mixing tip are hardened, the mixing tip is removed from the cartridge and replaced, and therefore the two component mixing apparatus is preferably configured such that the mixing tip can be removed from the cartridge by a simple operation.

The two component mixing apparatus according to patent literature 1 described above has a configuration in which the mixing tip and the cartridge are fixed by a coupling ring, and there is a possibility that the mixing tip cannot be easily removed from the cartridge.

The present invention has been made in view of the above, and an object of the present invention is to make it possible to firmly fix the mixing tip to the cartridge, and also remove the mixing tip from the cartridge by a simple operation.

Solution to Problem

According to an embodiment of the present invention, a locking member locks a mixing nozzle coupled to a cartridge that includes two syringes accommodating different materials, the mixing nozzle being configured to mix the materials pushed out from the two syringes in a nozzle and discharge the materials, the locking member including a support rod supported by the mixing nozzle so as to be displaceable in a direction orthogonal to a direction in which the nozzle extends; a first engaging part that protrudes from one end of the support rod toward an opposite side to the nozzle, and that is displaced toward another end of the support rod to be engaged with one of two horizontal parts that are provided so as to be bridged across the two syringes; a second engaging part that protrudes from a position of the support rod that is closer to the other end of support rod than the first engaging part, toward the opposite side to the nozzle, and that is inserted in between the two horizontal parts and displaced toward the other end of the support rod to be engaged with another one of the two horizontal parts; and an inclined part where the other end of the support rod is inclined toward the opposite side to the nozzle, the inclined part being provided in at least one of between the first engaging part and the second engaging part and between the second engaging part and the other end of the support rod.

Advantageous Effects of Invention

According to an embodiment of the present invention, it is possible to firmly fix the mixing tip to the cartridge, and also remove the mixing tip from the cartridge by a simple operation.

DESCRIPTION OF EMBODIMENTS

Figure 1:
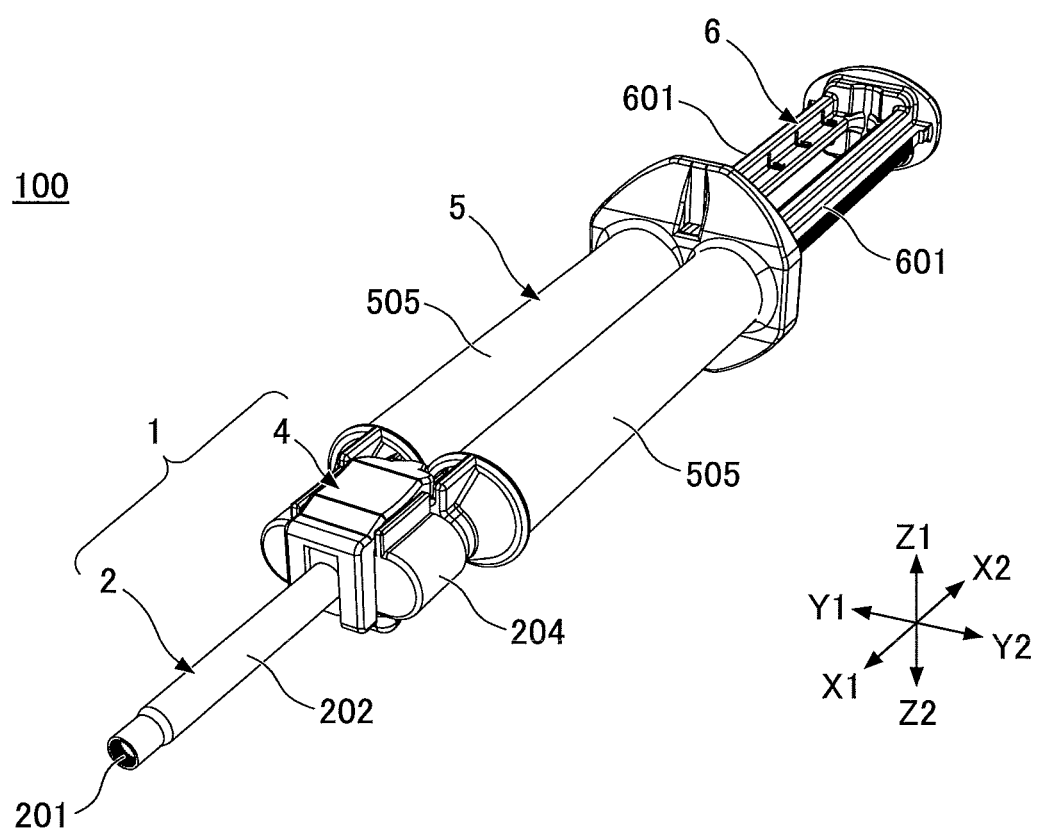
FIG. 1 is a perspective view of an example of a double syringe according to an embodiment.

In the following, a description is given of embodiments for carrying out the present invention, by referring to the drawings. In the drawings, the same reference numerals are applied to the same constituent elements, and overlapping descriptions may be omitted.

<Overall Configuration of Double Syringe>

Figure 2:
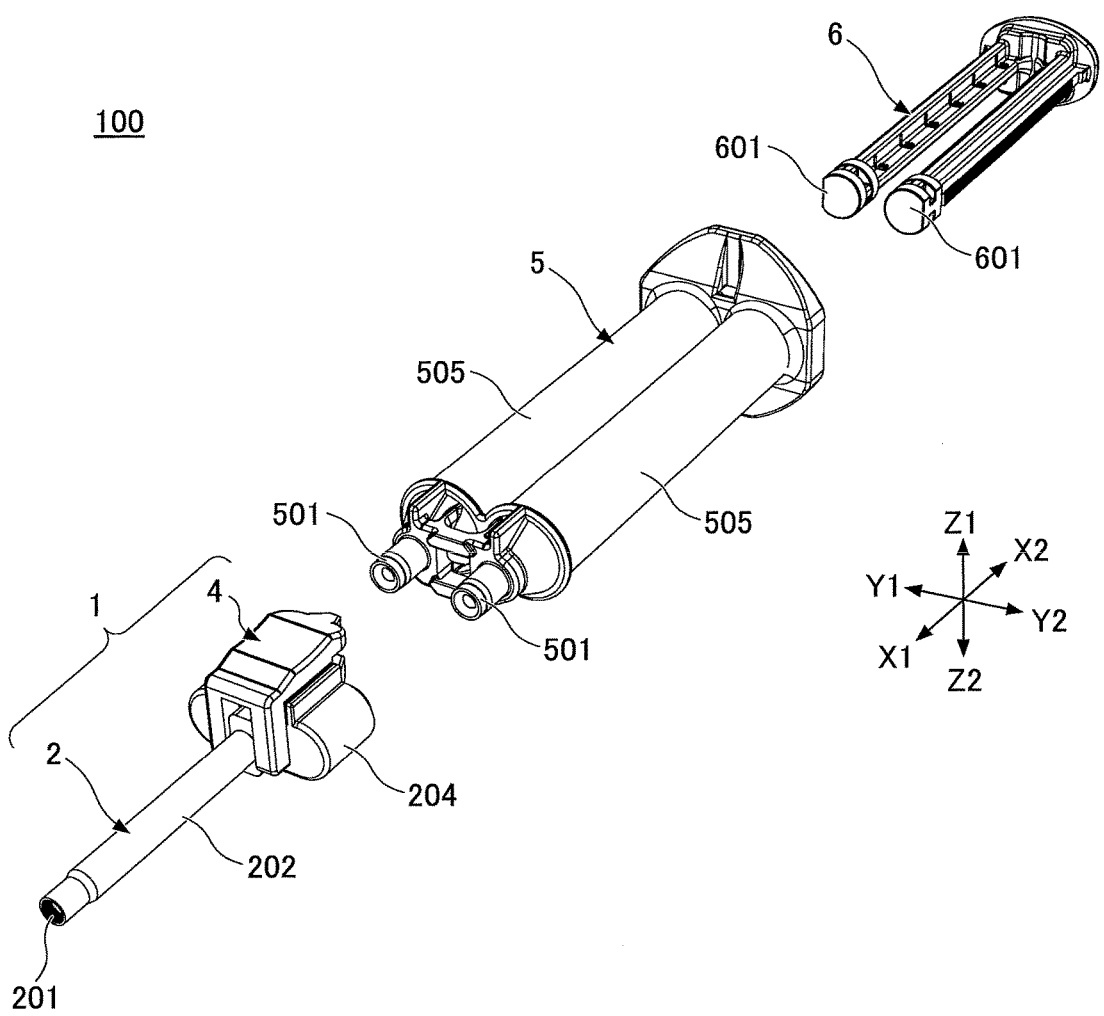
FIG. 2 is an exploded perspective view of an example of a double syringe according to an embodiment.

First, a description is given of the overall configuration of a double syringe 100 according to the present embodiment, based on FIGS. 1 and 2. FIG. 1 is a perspective view of the double syringe 100 according to an embodiment. Furthermore, FIG. 2 is an exploded perspective view of the double syringe 100 according to an embodiment.

Note that in the drawings described below, an X1X2 direction is the longitudinal direction of the double syringe 100. Furthermore, a Y1Y2 direction is the width direction of the double syringe 100, and a Z1Z2 direction is the height direction of the double syringe 100. In the following descriptions, the Z1 direction of the Z1Z2 direction may be referred to as up, and the Z2 direction of the Z1Z2 direction may be referred to as down.

As indicated in FIGS. 1 and 2, the double syringe 100 includes a mixing tip 1, a cartridge 5, and a plunger 6.

The mixing tip 1 includes a mixing nozzle 2 and a locking member 4, and the mixing tip 1 is detachably attached to the cartridge 5.

The mixing nozzle 2 includes a coupling cover 204 coupled to spouts 501 of the cartridge 5, and a nozzle 202 extending in the X1 direction from the coupling cover 204. The mixing nozzle 2 is fixed to the cartridge 5 by the locking member 4, in a state where the coupling cover 204 is coupled to the spouts 501 of the cartridge 5.

The mixing nozzle 2 mixes two types of materials extruded from the spouts 501 of the cartridge 5 by the plunger 6, with a mixing element provided in the nozzle 202, and discharges the materials from a discharging outlet 201 provided in the nozzle 202.

The locking member 4 is provided on the coupling cover 204 of the mixing nozzle 2 in a displaceable manner along the Z1Z2 direction, and the locking member 4 fixes the mixing nozzle 2 to the cartridge 5 in a state where the coupling cover 204 is coupled to the spouts 501 of the cartridge 5.

The cartridge 5 includes two syringes 505 for accommodating different materials. The syringe 505 includes a cylindrical material containing space inside, and has the spout 501 on one end and an opening in which a pusher 601 of the plunger 6 is inserted on the other end. As the pushers 601 of the plunger 6 are pushed into the cartridge 5 from openings of the syringes 505, the materials accommodated inside the cartridge 5 are pushed out from the spouts 501.

The plunger 6 includes two pushers 601 that are inserted in the two syringes 505 of the cartridge 5. As the pushers 601 are pushed into the syringes 505 by being depressed in the X1 direction, the plunger 6 pushes out the materials accommodated in the syringe 505 from the spouts 501.

The double syringe 100 has the above configuration, and as the plunger 6 is pushed into the cartridge 5, the materials pushed out from the two syringes 505 of the cartridge 5 are mixed in the mixing nozzle 2 and discharged from the discharging outlet 201.

<Configuration of Units of Double Syringe>

Next, a description is given of the configuration of each of the units of the double syringe 100 based on drawings.

(Mixing Nozzle)

Figure 3A:
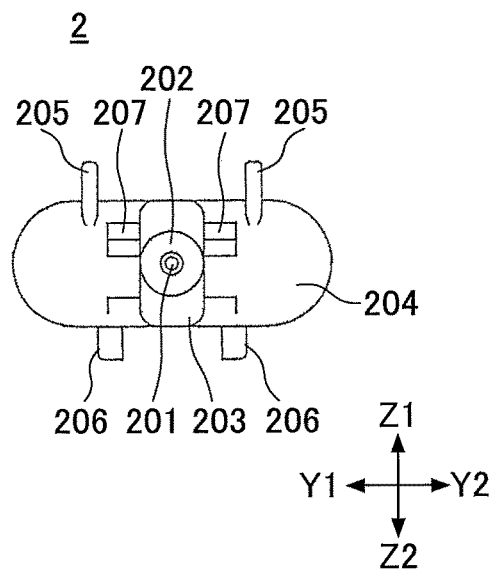
FIG. 3A is a left side view of an example of a mixing nozzle according to an embodiment.
Figure 3B:
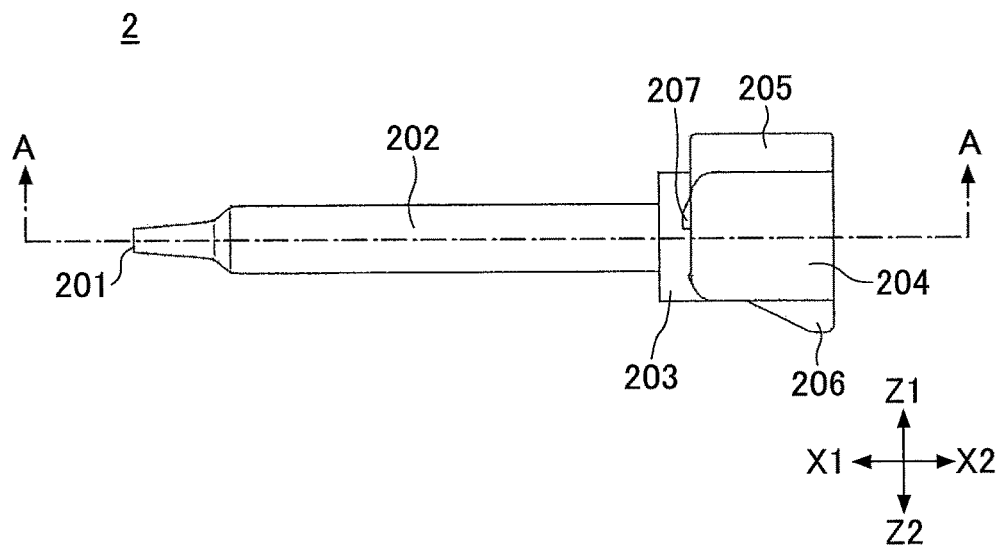
FIG. 3B is a front view of an example of a mixing nozzle according to an embodiment.
Figure 3C:
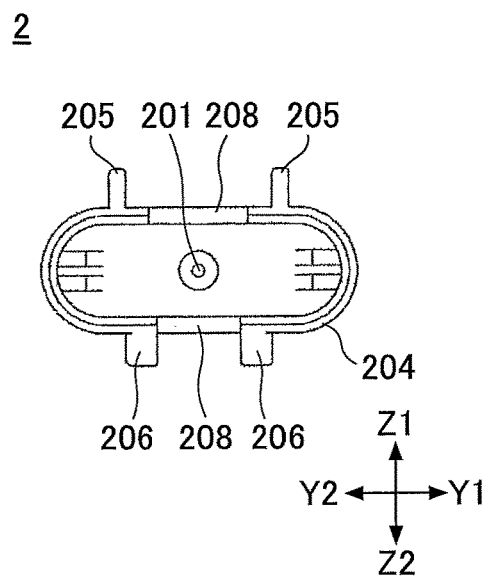
FIG. 3C is a right side view of an example of a mixing nozzle according to an embodiment.
Figure 3D:
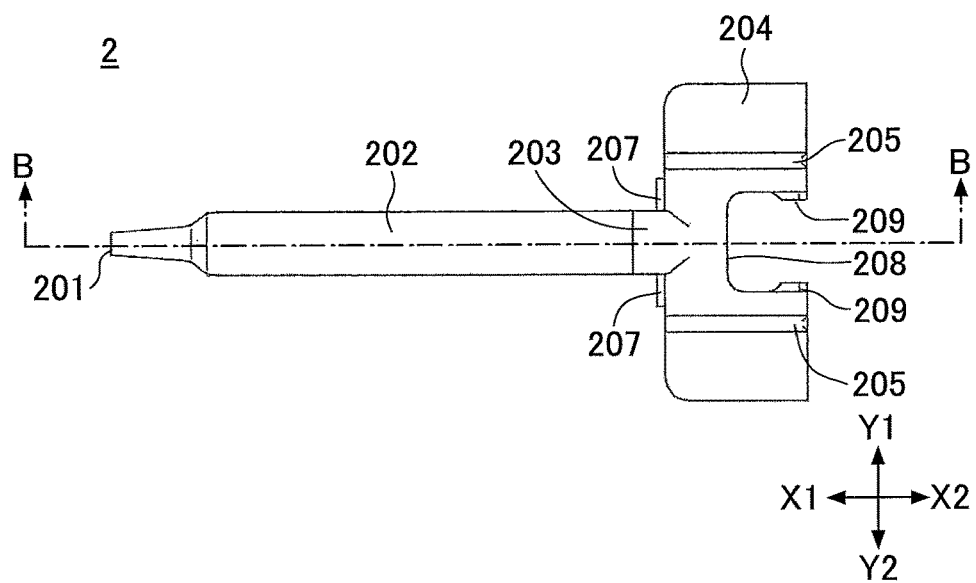
FIG. 3D is a top view of an example of a mixing nozzle according to an embodiment.
Figure 4A:
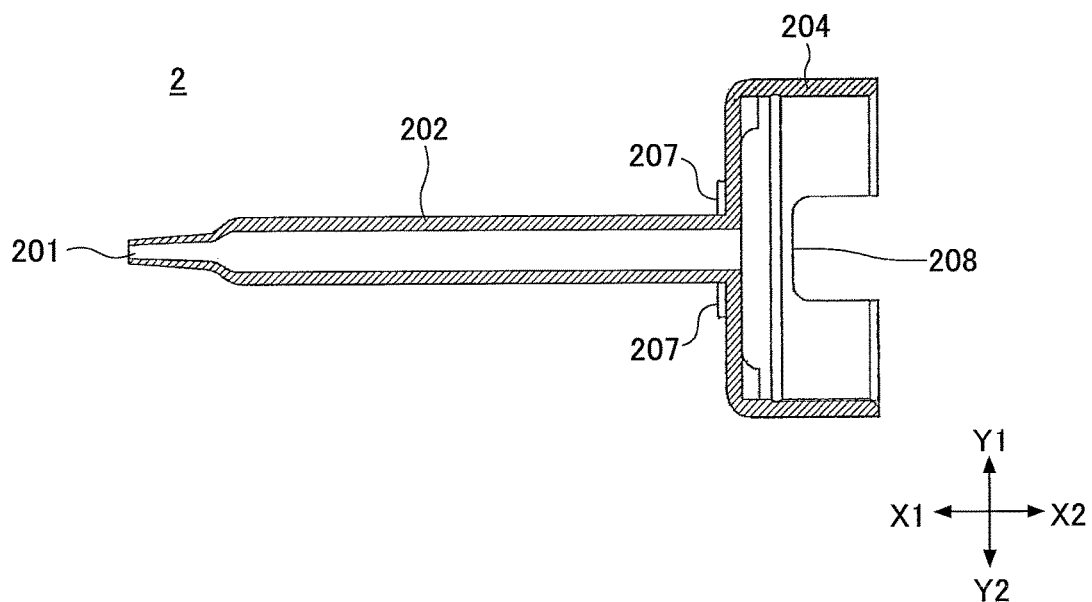
FIG. 4A is a cross-sectional view cut along a line A-A in FIG. 3B.
Figure 4B:
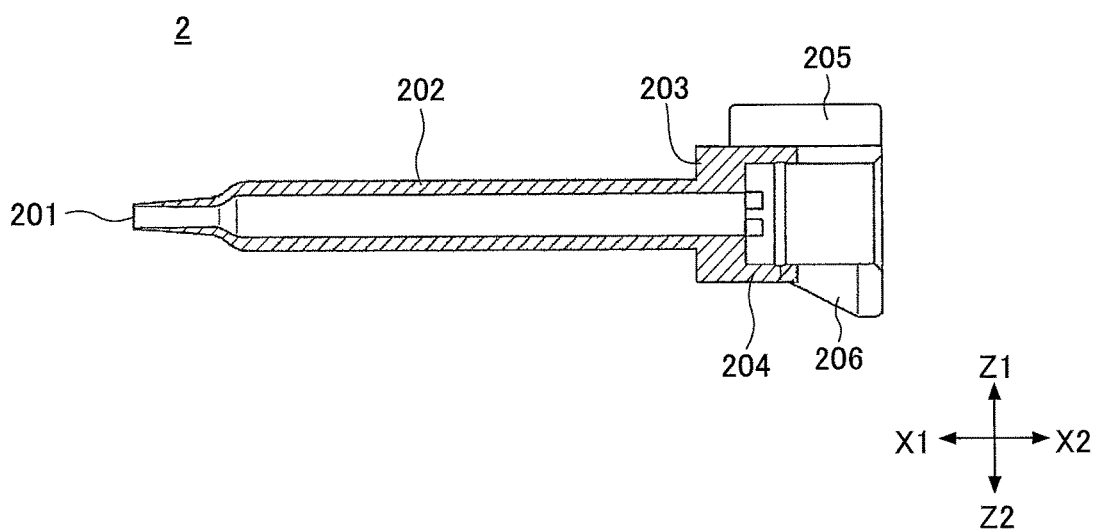
FIG. 4B is a cross-sectional view cut along a line B-B in FIG. 3D.

FIGS. 3A through 3D are diagrams indicating an example of the mixing nozzle 2 according to an embodiment; FIG. 3A is a left side view, FIG. 3B is a front view, FIG. 3C is a right side view, and FIG. 3D is a top view. Furthermore, FIGS. 4A and 4B are cross-sectional views indicating an example of the mixing nozzle 2 according to an embodiment; FIG. 4A is a cross-sectional view cut along a line A-A in FIG. 3B, and FIG. 4B is a cross-sectional view cut along a line B-B in FIG. 3D.

As indicated in FIGS. 3 and 4, the mixing nozzle 2 includes the nozzle 202 and the coupling cover 204. A mixing element is provided inside the nozzle 202 and the coupling cover 204, and the nozzle 202 and the coupling cover 204 are coupled to the spouts 501 of the cartridge 5.

The nozzle 202 is a hollow, cylindrical tube including the discharging outlet 201 at one end, and is provided so as to extend in the X1 direction from the coupling cover 204. The coupling cover 204 covers the syringe bearings of the mixing element provided inside, and is coupled to the cartridge 5 together with the mixing element.

(Mixing Element)

Figure 5A:
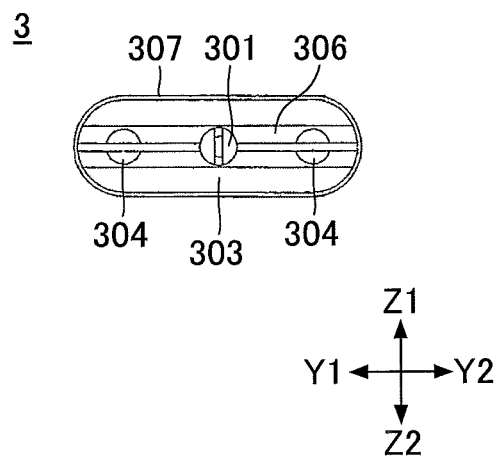
FIG. 5A is a left side view of an example of a mixing element according to an embodiment.
Figure 5B:
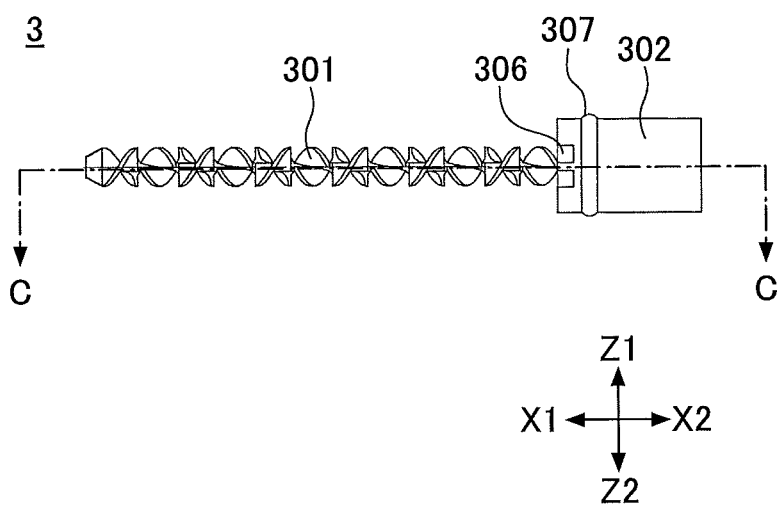
FIG. 5B is a front view of an example of a mixing element according to an embodiment.
Figure 5C:
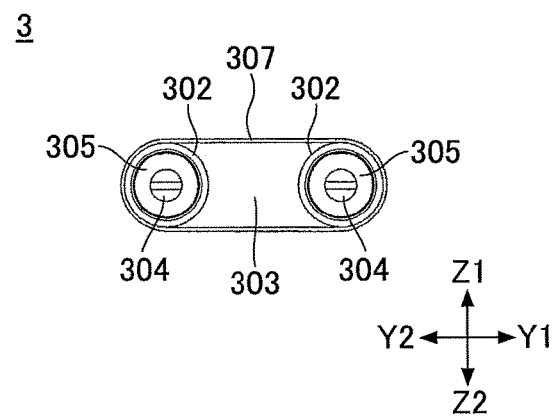
FIG. 5C is a right side view of an example of a mixing element according to an embodiment.
Figure 6:
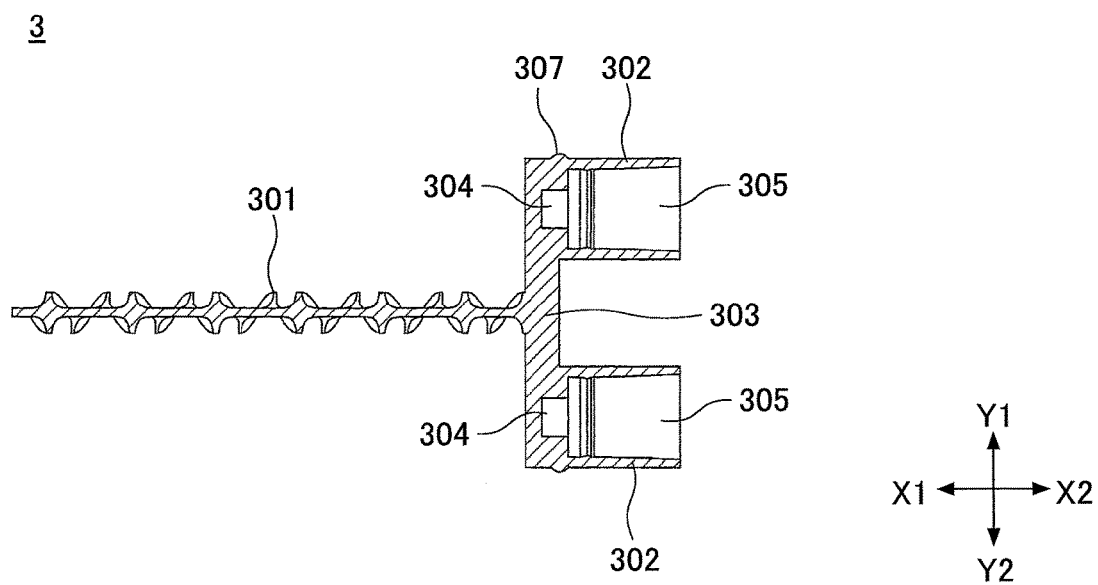
FIG. 6 is a cross-sectional view cut along a line C-C in FIG. 5B.

FIGS. 5A through 5C are diagrams indicating an example of a mixing element 3 according to an embodiment; FIG. 5A is a left side view, FIG. 5B is a front view, and FIG. 5C is a right side view. Furthermore, FIG. 6 is a cross-sectional view cut along a line C-C in FIG. 5B.

The mixing element 3 includes a mixing member 301, two syringe bearings 302, and a coupling part 303 coupling the two syringe bearings 302.

On the mixing member 301, a plurality of feather members are arranged in the X1X2 direction, and the mixing member 301 is provided to extend in the X1X2 direction from the coupling part 303. The syringe bearing 302 has a cylindrical shape in which the internal diameter is substantially equal to the external diameter of the spout 501 of the cartridge 5, and an opening 304 is provided on the end part on the side of the mixing member 301, and an insertion slot 305 is provided on the end part on the side opposite to the mixing member 301.

The mixing element 3 is press fit in the mixing nozzle 2 such that the mixing member 301 is inserted in the nozzle 202 of the mixing nozzle 2, and the syringe bearings 302 and the coupling part 303 are covered by the coupling cover 204 of the mixing member 301.

As the spouts 501 of the cartridge 5 are inserted in the syringe bearings 302 of the mixing element 3, the mixing nozzle 2 and the mixing element 3 are coupled to the cartridge 5.

When the plunger 6 is depressed in a state where the mixing nozzle 2 and the mixing element 3 are coupled to the cartridge 5, the materials, which are pushed out from the syringes 505, are injected inside the mixing nozzle 2 from the spouts 501 through the openings 304 of the syringe bearings 302.

On the surface of the coupling part 303 of the mixing element 3 on the side of the mixing member 301, there is provided a groove 306 that extends in the Y1Y2 direction in communication with the openings 304 of the syringe bearings 302. The groove 306 forms a flow path through which the materials pass between the coupling cover 204 of the mixing nozzle 2 and the mixing element 3, and the materials, which are injected from the openings 304 of the syringe bearings 302, pass through the groove 306 to be guided to the nozzle 202 of the mixing nozzle 2.

The two types of materials, which are pushed out form the two syringes 505 and guided to the nozzle 202 of the mixing nozzle 2, are mixed by the mixing member 301 while passing through the nozzle 202, and are discharged from the discharging outlet 201 of the mixing nozzle 2.

Furthermore, on the outer periphery of the syringe bearings 302 and the coupling part 303 of the mixing element 3, there is provided a ring-shaped protruding part 307 that protrudes in a ring shape. The ring-shaped protruding part 307 is in close contact with the inner wall surface of the coupling cover 204 of the mixing nozzle 2, and prevents the materials, which are passing through the groove 306, from leaking out of the part between the mixing nozzle 2 and the mixing element 3.

(Cartridge)

Figure 7A:
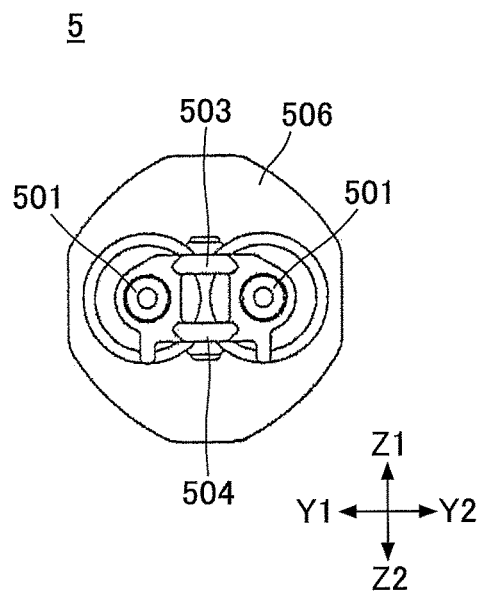
FIG. 7A is a left side view of an example of a cartridge according to an embodiment.
Figure 7B:
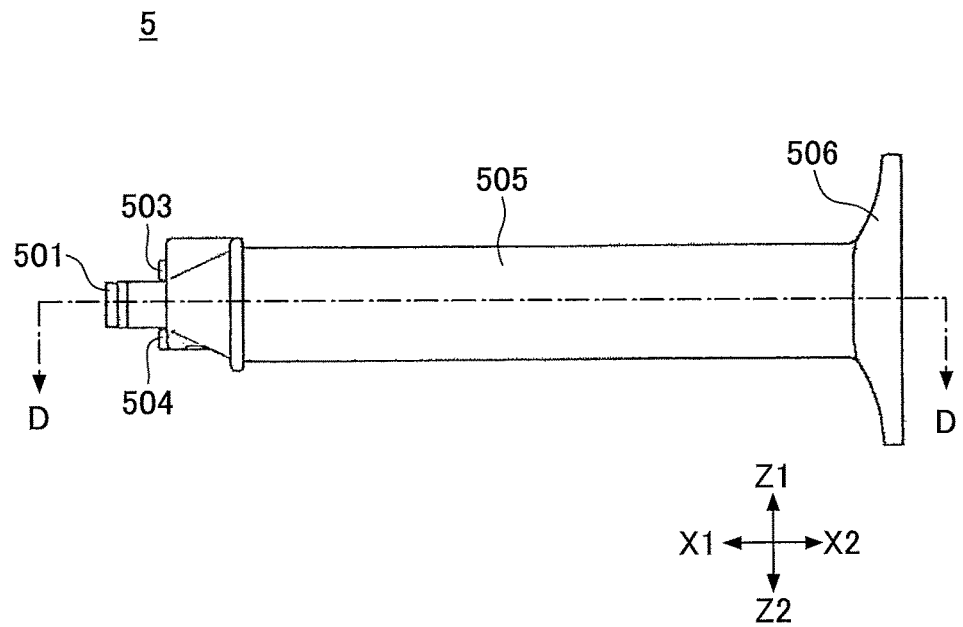
FIG. 7B is a front view of an example of a cartridge according to an embodiment.
Figure 7C:
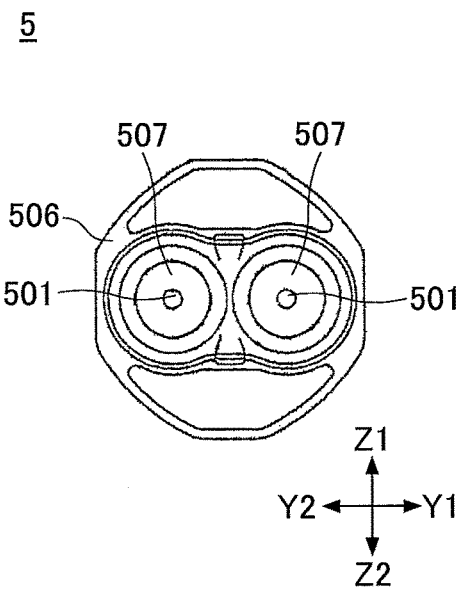
FIG. 7C is a right side view of an example of a cartridge according to an embodiment.
Figure 7D:
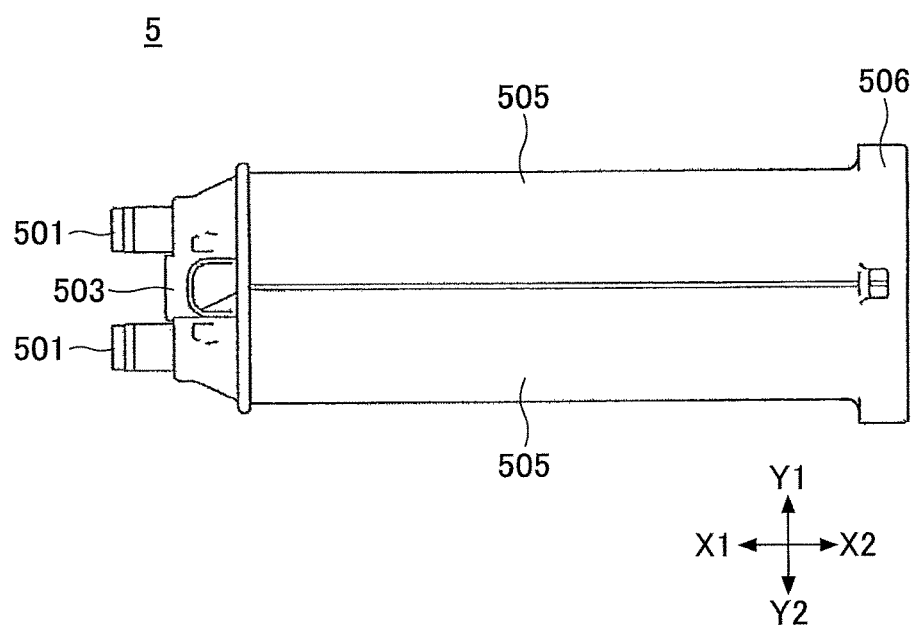
FIG. 7D is a top view of an example of a cartridge according to an embodiment.
Figure 8:
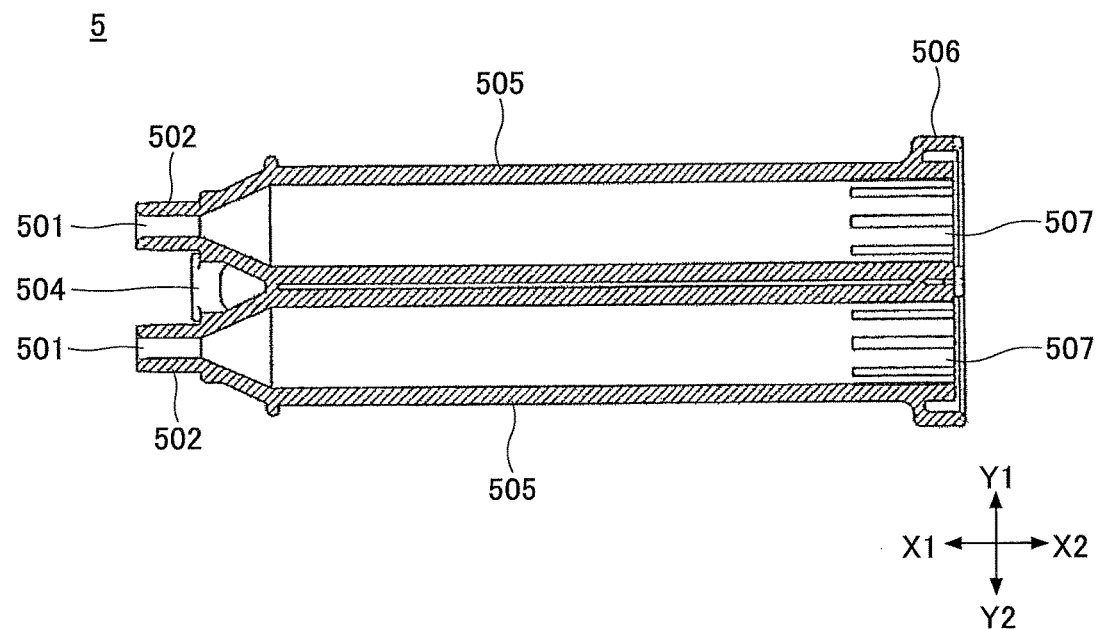
FIG. 8 is a cross-sectional view cut along a line D-D in FIG. 7B.

FIGS. 7A through 7D are diagrams indicating an example of the cartridge 5 according to an embodiment; FIG. 7A is a left side view, FIG. 7B is a front view, FIG. 7C is a right side view, and FIG. 7D is a top view. Furthermore, FIG. 8 is a cross-sectional view cut along a line D-D in FIG. 7B.

The cartridge 5 includes two hollow, cylindrical syringes 505 for accommodating different materials, and a flange part 506 onto which fingers are hitched when pushing the plunger 6 into the syringes 505. Each of the two syringes 505 includes the spout 501 at one end and a plunger insertion slot 507 on the other end. The two syringes 505 are arranged side by side in parallel. The pushers 601 of the plunger 6 are inserted in the plunger insertion slots 507 of the syringes 505.

The cartridge 5 is coupled to the mixing nozzle 2 and the mixing element 3 as the spouts 501 of the syringes 505 are inserted in the syringe bearings 302 of the mixing element 3. When the plunger 6 is depressed in a state where the mixing nozzle 2, the mixing element 3, and the cartridge 5 are coupled to each other, the materials accommodated in the accommodating units of the syringes 505 are pushed out to the mixing nozzle 2 from the spouts 501.

Furthermore, the cartridge 5 includes a pair of horizontal parts 503, 504 that are provided so as to be bridged across the spouts 501 of the two syringes 505, and that engage with the locking member 4. In the following, the upper side of the pair of horizontal parts 503, 504 is described as the first horizontal part 503, and the lower side of the pair of horizontal parts 503, 504 is described as the second horizontal part 504.

(Locking Member)

Figure 9A:
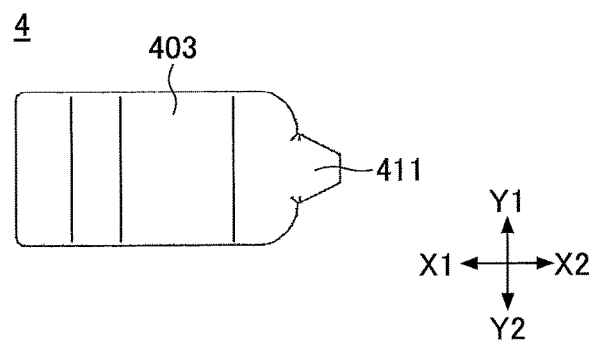
FIG. 9A is a top view of an example of a locking member a according to an embodiment.
Figure 9B:
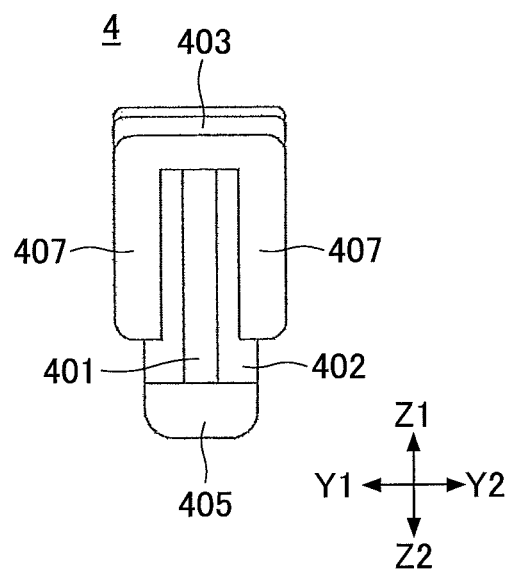
FIG. 9B is a left side view of an example of a locking member a according to an embodiment.
Figure 9C:
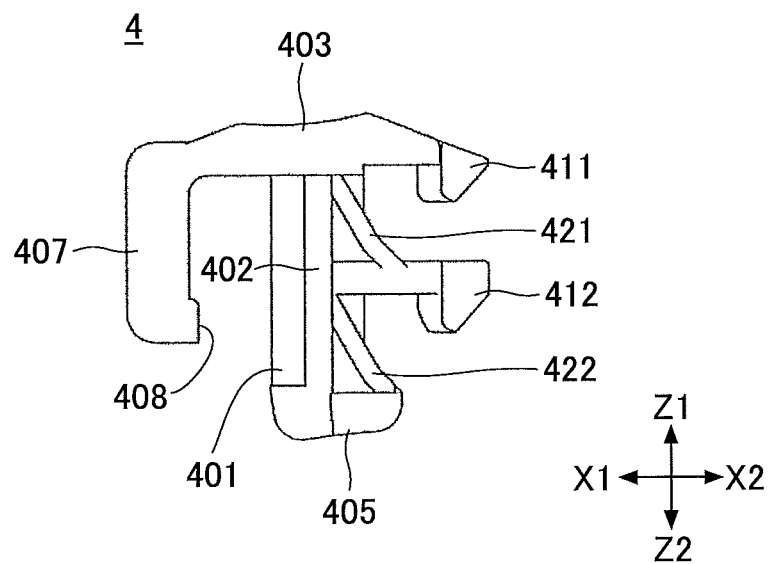
FIG. 9C is a front view of an example of a locking member a according to an embodiment.
Figure 9D:
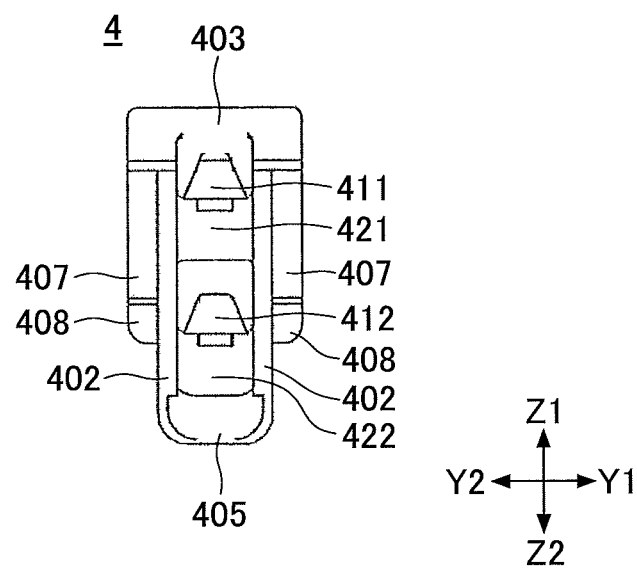
FIG. 9D is a right side view of an example of a locking member a according to an embodiment.
Figure 9E:
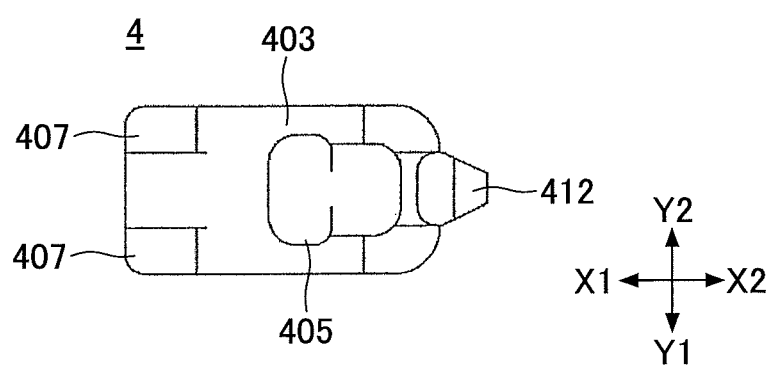
FIG. 9E is a bottom view of an example of a locking member a according to an embodiment.

FIGS. 9A through 9E are diagrams indicating an example of the locking member 4 according to an embodiment; FIG. 9A is a top view, FIG. 9B is a left side view, FIG. 9C is a front view, FIG. 9D is a right side view, and FIG. 9E is a bottom view.

As indicated in FIG. 9, the locking member 4 includes a support rod 401, a top side pushing part 403, a bottom side pushing part 405, an arm part 407, a first engaging part 411, a second engaging part 412, a first inclined part 421, and a second inclined part 422. The locking member 4 is provided on the mixing nozzle 2, fixes the mixing nozzle 2 and the mixing element 3 to the cartridge 5.

The support rod 401 is inserted in a support groove 208 provided in the coupling cover 204 of the mixing nozzle 2 indicated in FIG. 3D. The support rod 401 is supported by the mixing nozzle 2 so as to be displaceable in the Z1Z2 direction. The support rod 401 includes a rail part 402 protruding in the Y1 direction and the Y2 direction. As the rail part 402 is locked by locking claws 209 provided in the support groove 208, the support rod 401 is prevented from being removed from the mixing nozzle 2 in the X2 direction.

As indicated in FIG. 9, at the top end and the bottom end of the support rod 401, the plate-like top side pushing part 403 and the bottom side pushing part 405 are respectively provided. The top surface of the top side pushing part 403 and the bottom surface of the bottom side pushing part 405 have a curved shape so as to be easily pushed by fingers.

Two arm parts 407 protruding in the Z2 direction are provided on the end part of the top side pushing part 403 in the X1 direction. The two arm parts 407 are spaced apart in the Y1Y2 direction, and each of the aim parts 407 has a projection part 408 projecting in the X2 direction at the bottom end part.

In a state where the support rod 401 is inserted in the support groove 208 of the mixing nozzle 2, the arm parts 407 pinch the coupling cover 204 of the mixing nozzle 2 in between the support rod 401 and the aim parts 407. Furthermore, in this state, the aim parts 407 pinch the nozzle 202 of the mixing nozzle 2 and a projection part 203 protruding in the X1 direction from the coupling cover 204 and extending in the Z1Z2 direction, in between the aim parts 407.

As indicated in FIG. 3, on the top surface of the coupling cover 204 of the mixing nozzle 2, there is provided an upper guide part 205, which protrudes in the Z1 direction in parallel to the X1X2 direction and which guides the side surface of the top side pushing part 403 of the locking member 4. Furthermore, on the bottom surface of the coupling cover 204, there is provided a lower guide part 206, which protrudes in the Z2 direction and which guides the support rod 401 and the bottom side pushing part 405 of the locking member 4. Furthermore, on the coupling cover 204 of the mixing nozzle 2, there is provided a locking projection 207 protruding toward the nozzle 202 for locking the projection parts 408 of the arm parts 407, such that the locking member 4 does not come off the mixing nozzle 2 in the Z1 direction.

As described above, the locking member 4 is supported in a displaceable manner in the Z1Z2 direction, as the support rod 401 is inserted in the support groove 208 of the mixing nozzle 2. The locking member 4 is displaced in the Z2 direction as the top side pushing part 403 is pushed in the Z2 direction, and the locking member 4 is displaced in the Z1 direction as the bottom side pushing part 405 is pushed in the Z1 direction. Here, the locking member 4 is movable in a range in the Z1Z2 direction, from a position where the button surface of the top side pushing part 403 contacts the top surface of the coupling cover 204 of the mixing nozzle 2, to a position where the projection parts 408 of the arm parts 407 are locked to the locking projection 207 of the mixing nozzle 2.

Furthermore, as indicated in FIG. 9, there is provided the first engaging part 411 protruding in the X2 direction, at the top end of the support rod 401 of the locking member 4. Furthermore, similarly, there is provided the second engaging part 412 protruding in the X2 direction, at the bottom end of the first engaging part 411 of the support rod 401.

As the locking member 4 is displaced by being pushed in the Z2 direction, in a state where the mixing nozzle 2 and the mixing element 3 are coupled to the cartridge 5, the first engaging part 411 and the second engaging part 412 are respectively engaged with the first horizontal part 503 and the second horizontal part 504 of the cartridge 5. As described above, as the first engaging part 411 is engaged with the first horizontal part 503, and the second engaging part 412 is engaged with the second horizontal part 504, the mixing nozzle 2 and the mixing element 3 are fixed in a state of being coupled to the cartridge 5.

Between the first engaging part 411 and the second engaging part 412, there is provided the first inclined part 421 in which the bottom end side is inclined toward the X2 direction. Furthermore, between the second engaging part 412 and the bottom side pushing part 405, there is provided the second inclined part 422 having the same shape as the first inclined part 421.

When the locking member 4 is pushed and displaced in the Z1 direction, from a state where the mixing nozzle 2 and the mixing element 3 are fixed to the cartridge 5, as the first engaging part 411 and the second engaging part 412 come off the first horizontal part 503 and the second horizontal part 504, and the mixing nozzle 2 and the mixing element 3 are released from a state of being fixed to the cartridge 5.

Here, when the locking member 4 is displaced in the Z1 direction, the first horizontal part 503 and the second horizontal part 504 of the cartridge 5 respectively contact the first inclined part 421 and the second inclined part 422, and a force is applied to the locking member 4 in the X1 direction. Therefore, the locking member 4 is displaced in the Z1 direction and the X1 direction with respect to the cartridge 5, such that the first inclined part 421 and the second inclined part 422 move along the first horizontal part 503 and the second horizontal part 504. Therefore, when the locking member 4 is pushed in the Z1 direction, the locking member 4 is displaced in the Z1 direction, and the mixing nozzle 2 and the mixing element 3 are also displaced in the X1 direction so as to be removed from the cartridge 5.

Figure 10:
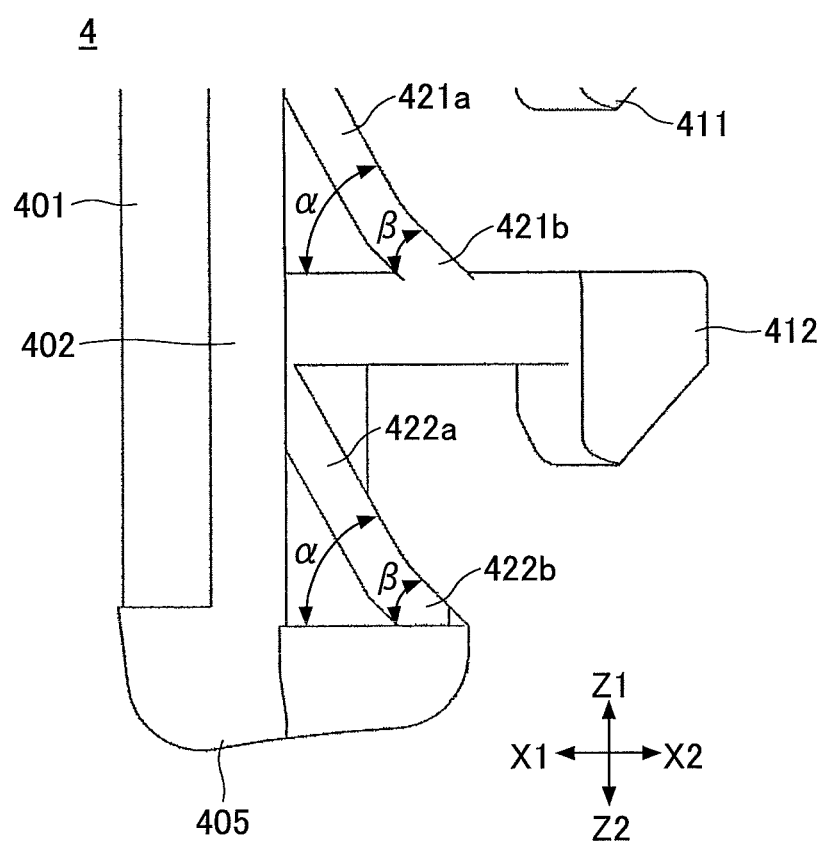
FIG. 10 is a partial enlarged view of an example of an example of a locking member according to an embodiment.

FIG. 10 is a partial enlarged view of an example of the locking member 4 according to an embodiment.

As indicated in FIG. 10, the first inclined part 421 includes an upper end side inclined part 421*a* that is inclined by a first inclined angle α with respect to the X1X2 direction, and a lower end side inclined part 421*b* that is inclined by a second inclined angle β that is smaller than the first inclined angle α with respect to the X1X2 direction. Furthermore, similarly, the second inclined part 422 includes an upper end side inclined part 422*a* that is inclined by the first inclined angle α with respect to the X1X2 direction, and a lower end side inclined part 422*b* that is inclined by the second inclined angle β that is smaller than the first inclined angle α with respect to the X1X2 direction.

The first inclined angle α is preferably made as large as possible, such that the locking member 4 can be smoothly displaced in the X1 direction by being pushed by the first horizontal part 503 and the second horizontal part 504, without having the first horizontal part 503 and the second horizontal part 504 of the cartridge 5 being caught by the upper end side inclined parts 421*a*, 422*a*, when the locking member 4 is pushed in the Z1 direction. Furthermore, the second inclined angle β is preferably made as small as possible, such that the displacement amount of the locking member 4 in the X1 direction is greater than the displacement amount of the locking member 4 in the Z1 direction.

Figure 11:
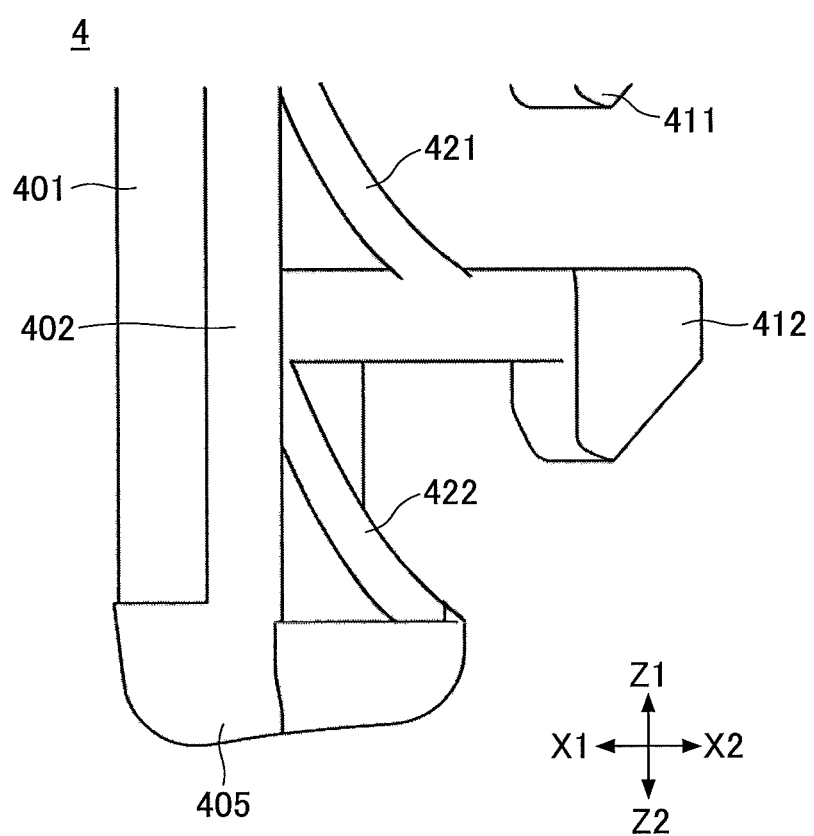
FIG. 11 is a partial enlarged view of an example of an example of a locking member according to an embodiment.

Note that in the present embodiment, the first inclined angle α is 60° and the second inclined angle β is 45°; however, different angles may be appropriately set according to the shapes, etc., of the locking member 4 and the cartridge 5. Furthermore, in the present embodiment, the first inclined part 421 and the second inclined part 422 are two inclined parts having different inclined angles; however, there may be three inclined parts having different inclined angles. Furthermore, as indicated in FIG. 11, the first inclined part 421 and the second inclined part 422 may have partially cylindrical shapes in which the inclined angle changes gradually.

<Attaching Mixing Tip to Cartridge>

Next, a description is given of a method attaching the mixing tip 1 formed of the mixing nozzle 2, the mixing element 3, and the locking member 4, to the cartridge 5.

Figure 12A:
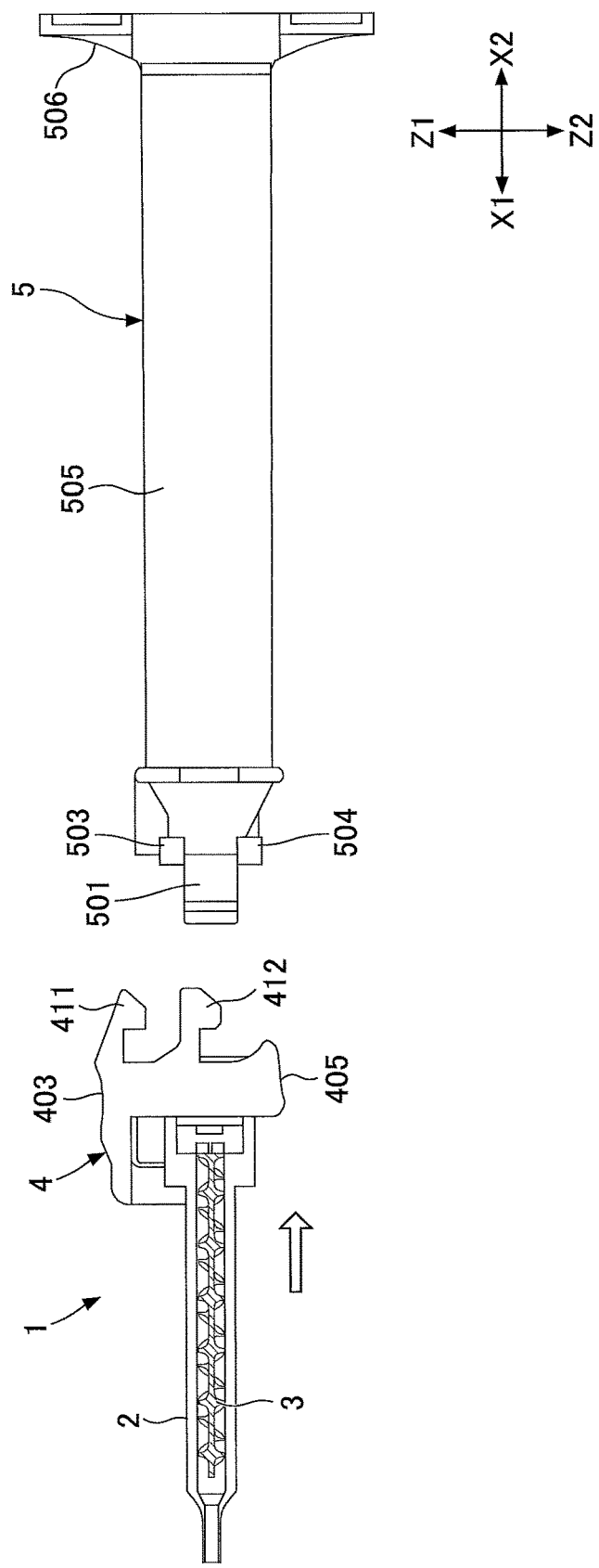
FIG. 12A is a diagram indicating an example of how a mixing tip is attached to a cartridge according to an embodiment.
Figure 12B:
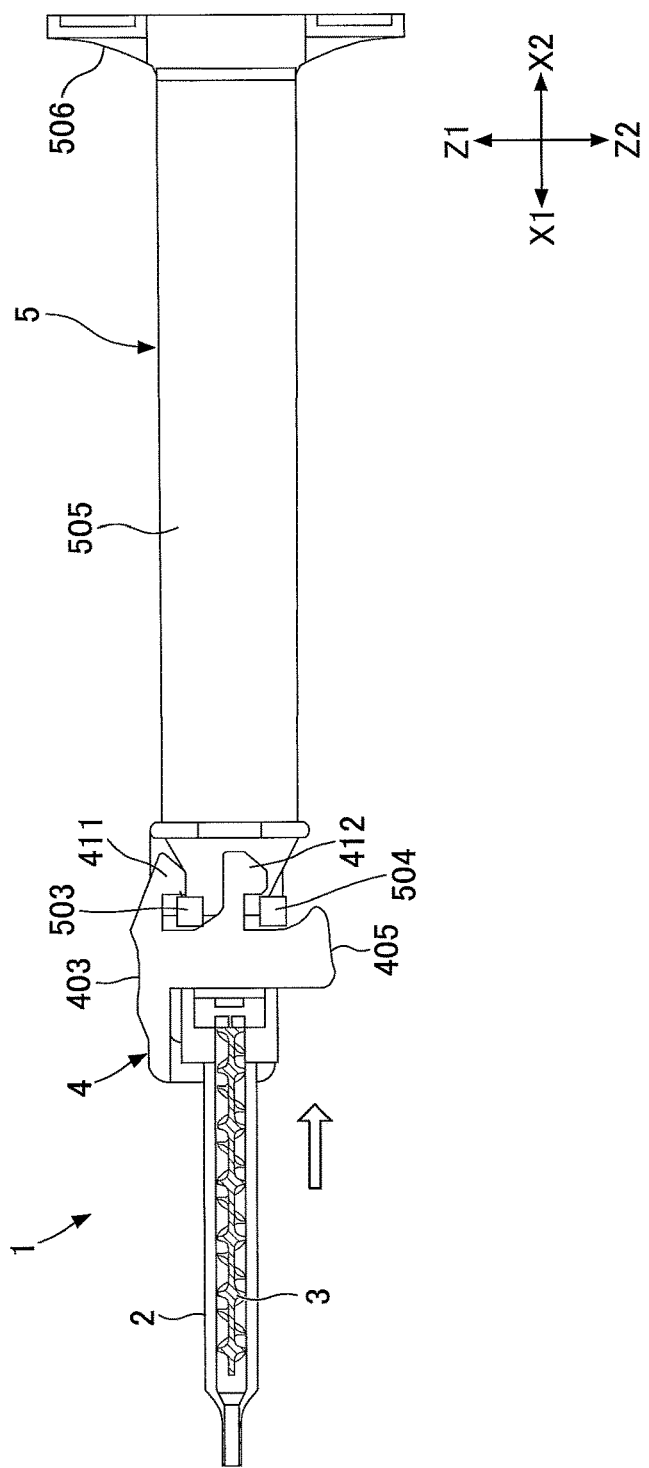
FIG. 12B is a diagram indicating an example of how a mixing tip is attached to a cartridge according to an embodiment.
Figure 12C:
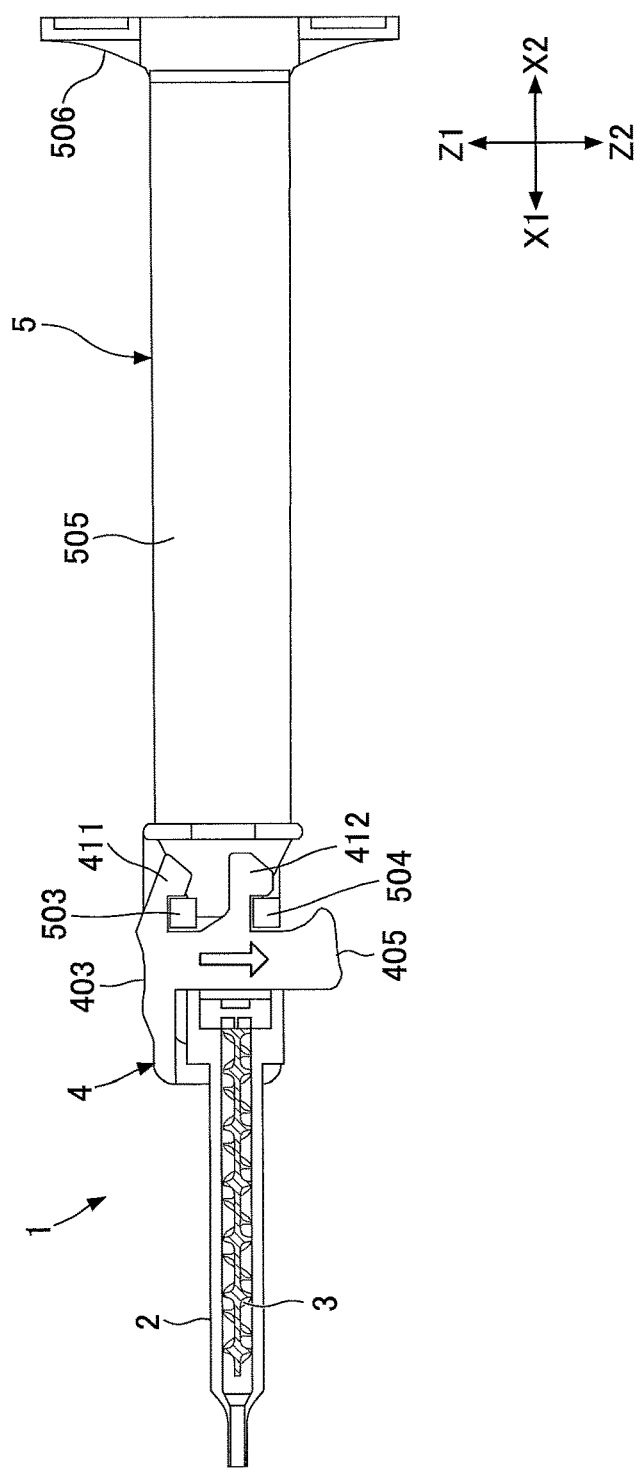
FIG. 12C is a diagram indicating an example of how a mixing tip is attached to a cartridge according to an embodiment.

FIGS. 12A through 12C are diagrams indicating an example of how the mixing tip 1 is attached to the cartridge 5 according to an embodiment.

When attaching the mixing tip 1 to the cartridge 5, first, as indicated in FIG. 12A, the positions of the syringe bearings 302 of the mixing element 3 and the positions of the spouts 501 of the cartridge 5 are matched, and the mixing tip 1 is brought near the cartridge 5.

Next, as indicated in FIG. 12B, the mixing tip 1 is moved further in the X2 direction, the spouts 501 of the cartridge 5 are inserted in the syringe bearings 302 of the mixing element 3, and the mixing tip 1 and the cartridge 5 are coupled to each other. At this time, the first engaging part 411 of the locking member 4 passes along the top side of the first horizontal part 503 of the cartridge 5, and the second engaging part 412 is inserted in between the first horizontal part 503 and the second horizontal part 504.

Next, as indicated in FIG. 12C, the top side pushing part 403 of the locking member 4 is pushed to be displaced in the Z2 direction, such that the first engaging part 411 is engaged with the first horizontal part 503 and the second engaging part 412 is engaged with the second horizontal part 504. In this way, the first engaging part 411 and the second engaging part 412 of the locking member 4 are respectively engaged with the first horizontal part 503 and the second horizontal part 504 of the cartridge 5, such that the mixing tip 1 is fixed to the cartridge 5 and the attachment is completed.

<Removing Mixing Tip from Cartridge>

Figure 13A:
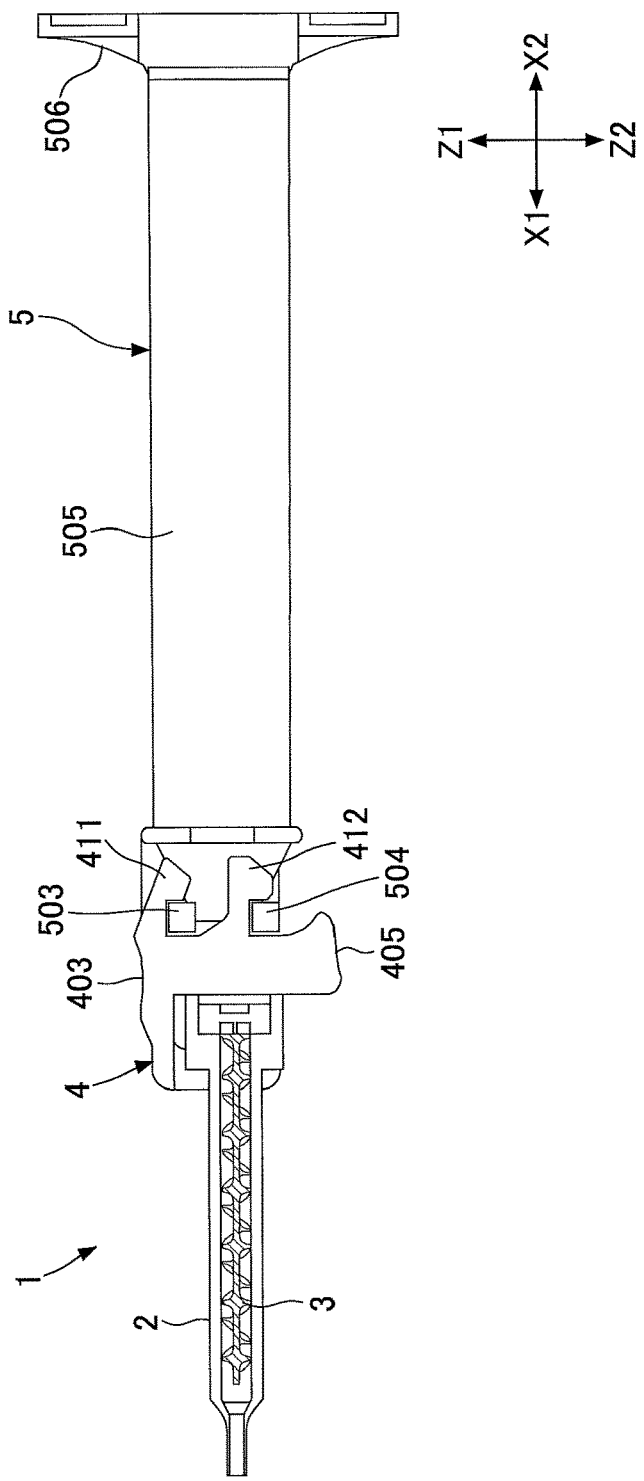
FIG. 13A is a diagram indicating an example of how a mixing tip is removed from a cartridge according to an embodiment.
Figure 13B:
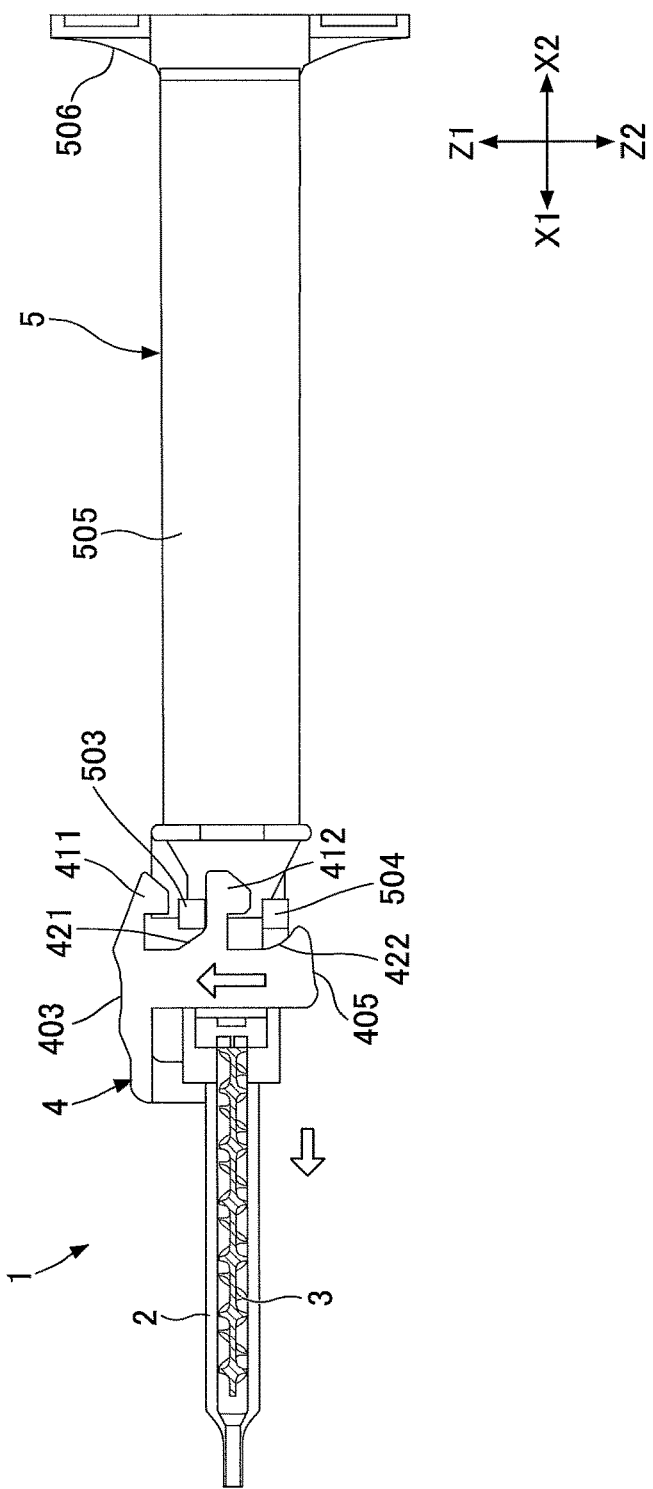
FIG. 13B is a diagram indicating an example of how a mixing tip is removed from a cartridge according to an embodiment.
Figure 13C:
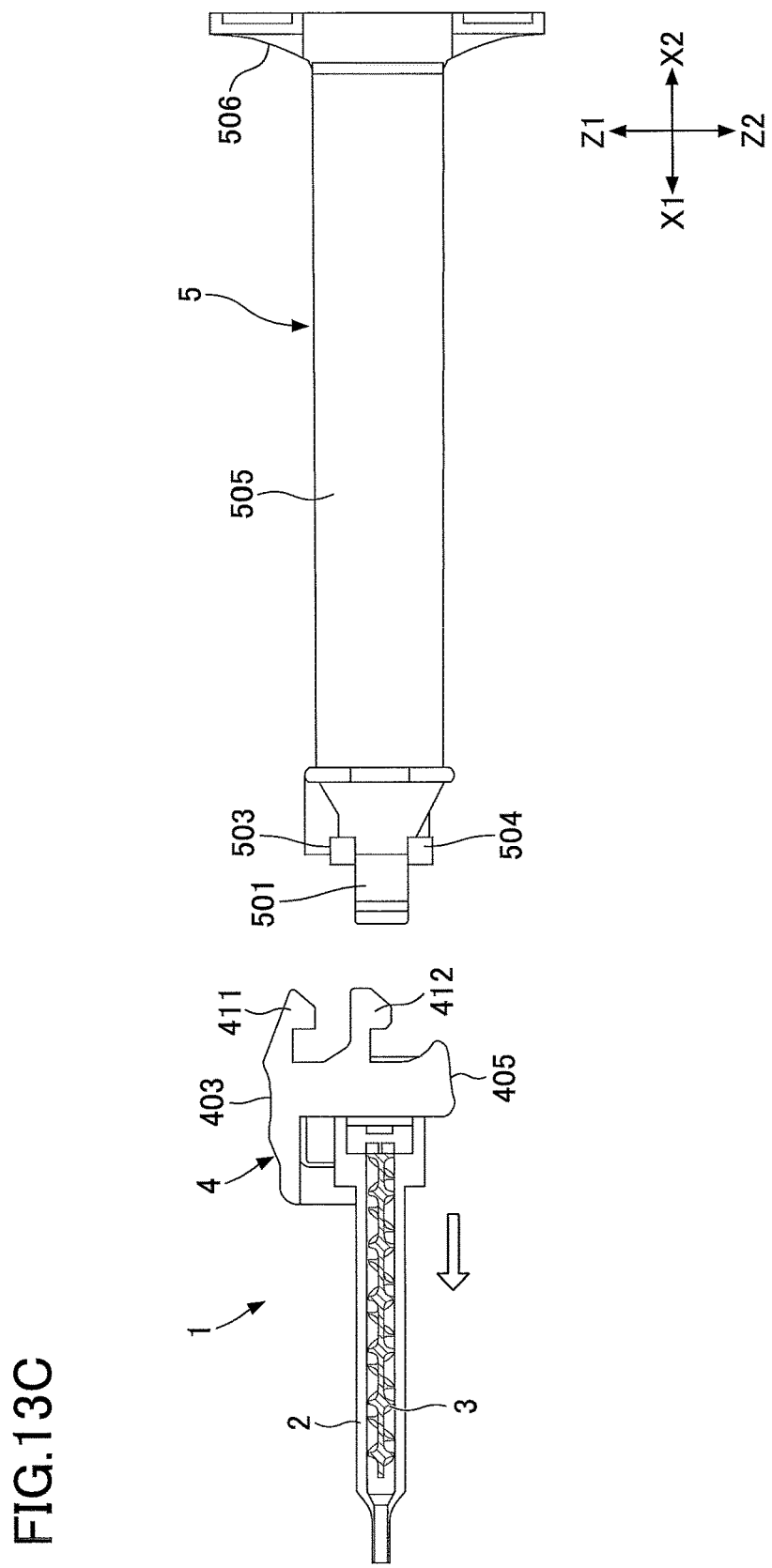
FIG. 13C is a diagram indicating an example of how a mixing tip is removed from a cartridge according to an embodiment.

FIGS. 13A through 13C are diagrams indicating an example of how the mixing tip 1 is removed from the cartridge 5 according to an embodiment.

In order to remove the mixing tip 1 attached to the cartridge 5 as indicated in FIG. 13A, first, as indicated in FIG. 13B, the bottom side pushing part 405 of the locking member 4 is pushed to be displaced in the Z1 direction.

When the locking member 4 is displaced in the Z1 direction, the first engaging part 411 and the second engaging part 412 come off from the first horizontal part 503 and the second horizontal part 504 of the cartridge 5, and are released from the engaged state. Furthermore, the first inclined part 421 and the second inclined part 422 of the locking member 4 are respectively depressed by the first horizontal part 503 and the second horizontal part 504 of the cartridge 5, the mixing tip 1 including the locking member 4 is displaced in the X1 direction, and the mixing tip 1 comes off the cartridge 5. However, in this state, the leading end parts of the spouts 501 of the cartridge 5 are still inserted in the syringe bearings 302 of the mixing element 3, and the mixing tip 1 is not completely removed from the cartridge 5.

Next, as indicated in FIG. 13C, by moving the mixing tip 1 in the X1 direction, the mixing tip 1 is completely removed from the cartridge 5.

As described above, by the locking member 4, the mixing tip 1, and the double syringe 100 according to the present embodiment, the mixing nozzle 2 and the mixing element 3 are firmly fixed to the cartridge 5. Furthermore, by a simple operation of pushing the locking member 4 upwards, the mixing nozzle 2 and the mixing element 3 can be easily removed from the cartridge 5.

The locking member, the mixing tip, and the double syringe according to an embodiment are described above; however, the present invention is not limited to the embodiments described above, and variations and modifications may be made without departing from the scope of the present invention.

The present international application claims the benefit of priority of Japanese Patent Application No. 2014-158717, filed on Aug. 4, 2014, the contents of which are incorporated herein by reference in their entirety.

REFERENCE SIGNS LIST 1 mixing tip
2 mixing nozzle
3 mixing element
4 locking member
401 support rod
5 cartridge
100 double syringe
202 nozzle
411 first engaging part
412 second engaging part
421 first inclined part
422 second inclined part
503 first horizontal part
504 second horizontal part
505 syringe

The invention claimed is:

1. A locking member that locks a mixing nozzle coupled to a cartridge that includes two syringes accommodating different materials, the mixing nozzle being configured to mix the materials pushed out from the two syringes in a nozzle and discharge the materials, the locking member comprising:

a support rod supported by the mixing nozzle so as to be displaceable in a direction orthogonal to a direction in which the nozzle extends, the support rod having a top end and a bottom end;
a first engaging part that protrudes from the top end of the support rod toward an opposite side to the nozzle, and that is displaced toward the bottom end of the support rod to be engaged with one of two horizontal parts that are provided so as to be bridged across the two syringes;
a second engaging part that protrudes from a position of the support rod that is closer to the bottom end of the support rod than the first engaging part, toward the opposite side to the nozzle, and that is inserted in between the two horizontal parts and displaced toward the bottom end of the support rod to be engaged with another one of the two horizontal parts;
a first inclined part that is provided between the first engaging part and the second engaging part;
a second inclined part that is provided between the second engaging part and the bottom end of the support rod, wherein
each of the first inclined part and the second inclined part has an upper end that connects with the support rod at a first inclined angle ($\alpha$) with respect to the direction in which the nozzle extends, and
the first inclined part has a lower end that is inclined toward the opposite side to the nozzle and connects with the second engaging part,
the second inclined part has a lower end that is inclined toward the opposite side to the nozzle and connects with the bottom end of the support rod, and
the lower end of the first inclined part and of the second inclined part is connected to the second engaging part and the bottom end of the support rod, respectively, at a second inclined angle ($\beta$), smaller than the first inclined angle ($\alpha$), with respect to the direction in which the nozzle extends.

2. The locking member according to claim 1, wherein the first inclined part and/or the second inclined part has a partial cylindrical shape whose inclined angle gradually changes with respect to a protrusion direction in which the first engaging part and the second engaging part protrude, from the top end toward the bottom end of the support rod.

3. A mixing tip comprising:
the locking member according to claim 1; and
the mixing nozzle.

4. A double syringe comprising:
the mixing tip according to claim 3; and
the cartridge.

* * * * *